United States Patent
Field

(10) Patent No.: US 9,620,343 B1
(45) Date of Patent: Apr. 11, 2017

(54) BALANCED SAMPLE INTRODUCTION SYSTEM

(71) Applicant: Elemental Scientific, Inc., Omaha, NE (US)

(72) Inventor: Paul Field, Papillion, NE (US)

(73) Assignee: Elemental Scientific, Inc., Omaha, NE (US)

( * ) Notice: Subject to any disclaimer, the term of this patent is extended or adjusted under 35 U.S.C. 154(b) by 65 days.

(21) Appl. No.: 14/566,493

(22) Filed: Dec. 10, 2014

Related U.S. Application Data

(60) Provisional application No. 61/914,228, filed on Dec. 10, 2013, provisional application No. 61/915,244, filed on Dec. 12, 2013.

(51) Int. Cl.
*H01J 49/04* (2006.01)
*H01J 49/10* (2006.01)

(52) U.S. Cl.
CPC ........ *H01J 49/0422* (2013.01); *H01J 49/105* (2013.01)

(58) Field of Classification Search
CPC .. H01J 49/0422; H01J 49/0445; H01J 49/045; H01J 49/105; H01J 49/107; H01J 49/04; H01J 49/10; H01J 49/0431
See application file for complete search history.

(56) References Cited

U.S. PATENT DOCUMENTS

| | | | | |
|---|---|---|---|---|
| 5,867,262 A | * | 2/1999 | Etoh | G01N 35/08 250/288 |
| 6,207,954 B1 | * | 3/2001 | Andrien, Jr. | H01J 49/0009 250/282 |
| 7,265,362 B2 | * | 9/2007 | Bajic | H01J 49/044 250/423 R |
| 2003/0052269 A1 | * | 3/2003 | Apffel, Jr. | G01N 30/7266 250/288 |
| 2012/0160997 A1 | * | 6/2012 | Fink | H01J 49/10 250/282 |

\* cited by examiner

*Primary Examiner* — David E Smith
(74) *Attorney, Agent, or Firm* — Advent, LLP

(57) ABSTRACT

A system includes a first aerosolization device (e.g., a nebulizer and a spray chamber/desolvation device in fluid communication with the nebulizer) configured to furnish a first aerosol, and a second aerosolization device (e.g., a second nebulizer and a second spray chamber/desolvation device in fluid communication with the second nebulizer) configured to furnish a second aerosol. The first aerosolization device is balanced with the second aerosolization device. The system also includes an output coupled with the first aerosolization device and the second aerosolization device. The output is configured to supply at least one of the first aerosol or the second aerosol (e.g., to a torch). The system further includes a selection device coupling the first aerosolization device and the second aerosolization device to the output. The selection device is configured to selectively provide at least one of the first aerosol or the second aerosol to the output.

20 Claims, 9 Drawing Sheets

BALANCED SAMPLE INTRODUCTION SYSTEM

CROSS-REFERENCE TO RELATED APPLICATIONS

The present application claims the benefit under 35 U.S.C. §119(e) of U.S. Provisional Application Ser. No. 61/914,228, filed Dec. 10, 2013, and titled "BALANCED SAMPLE INTRODUCTION SYSTEM," and U.S. Provisional Application Ser. No. 61/915,244, filed Dec. 12, 2013, and titled "BALANCED SAMPLE INTRODUCTION SYSTEM." U.S. Provisional Application Ser. Nos. 61/914,228 and 61/915,244 are herein incorporated by reference in their entireties.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A system includes a first aerosolization device (e.g., a

DETAILED DESCRIPTION

Figure 1:
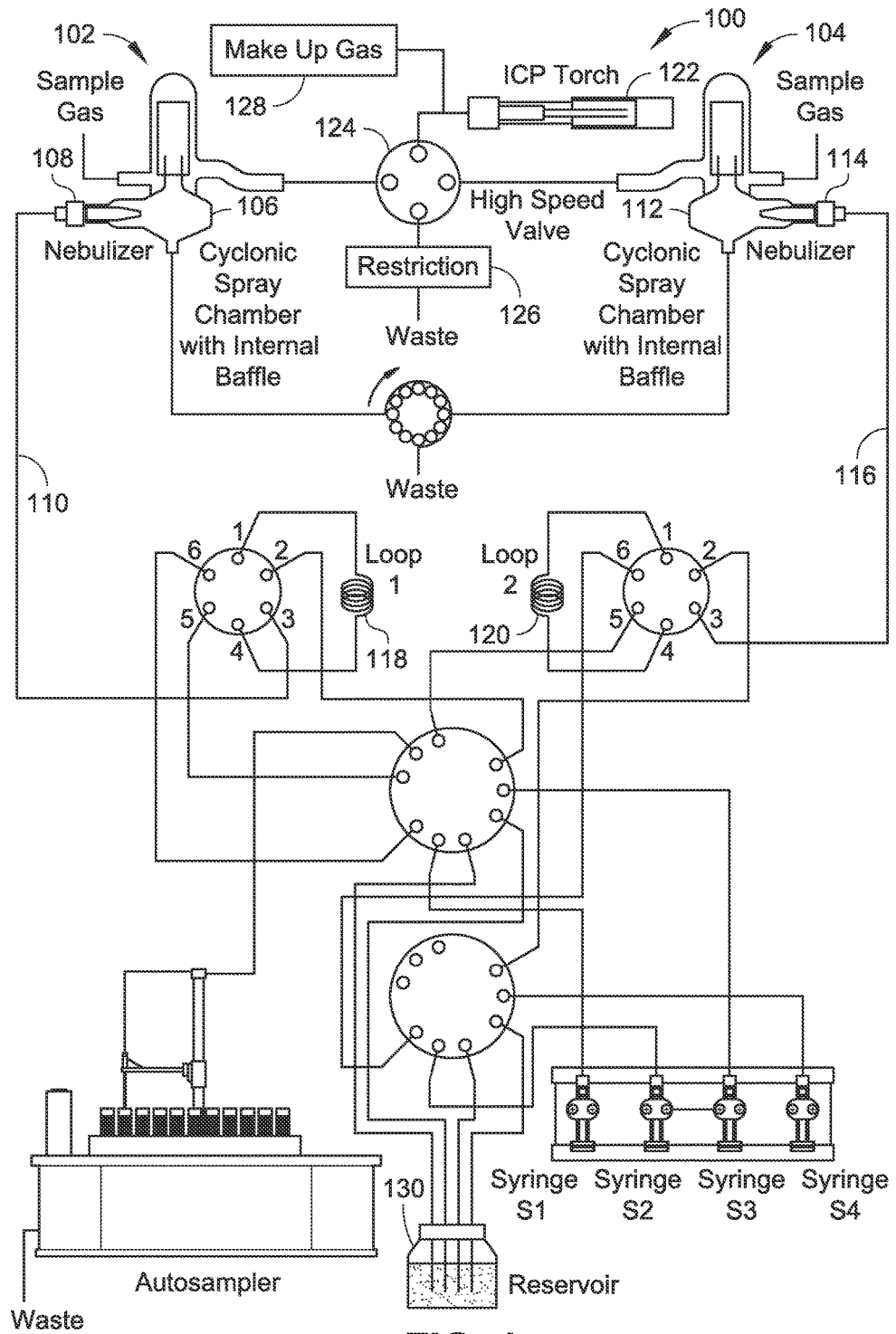
Figure 2:
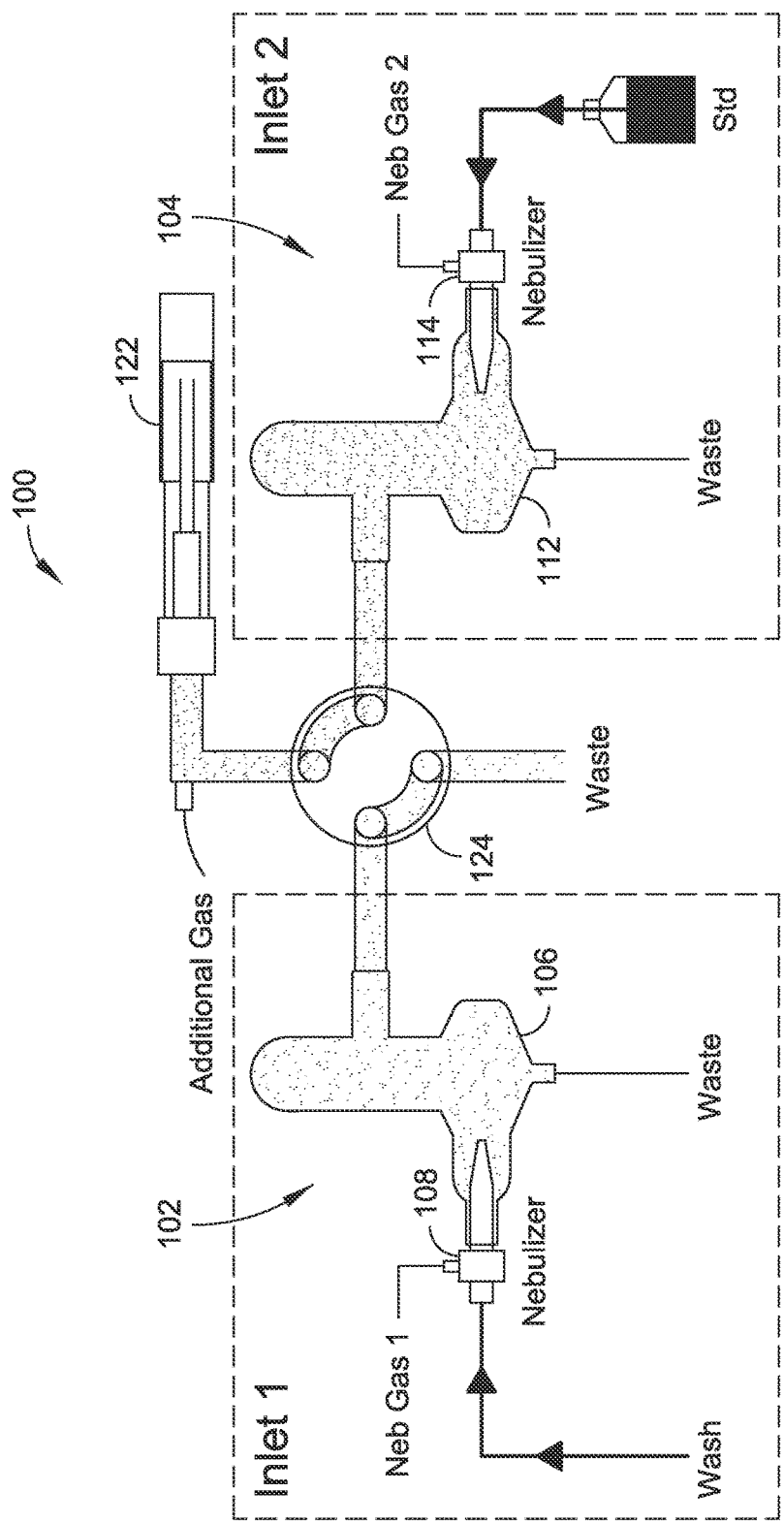
Figure 3:
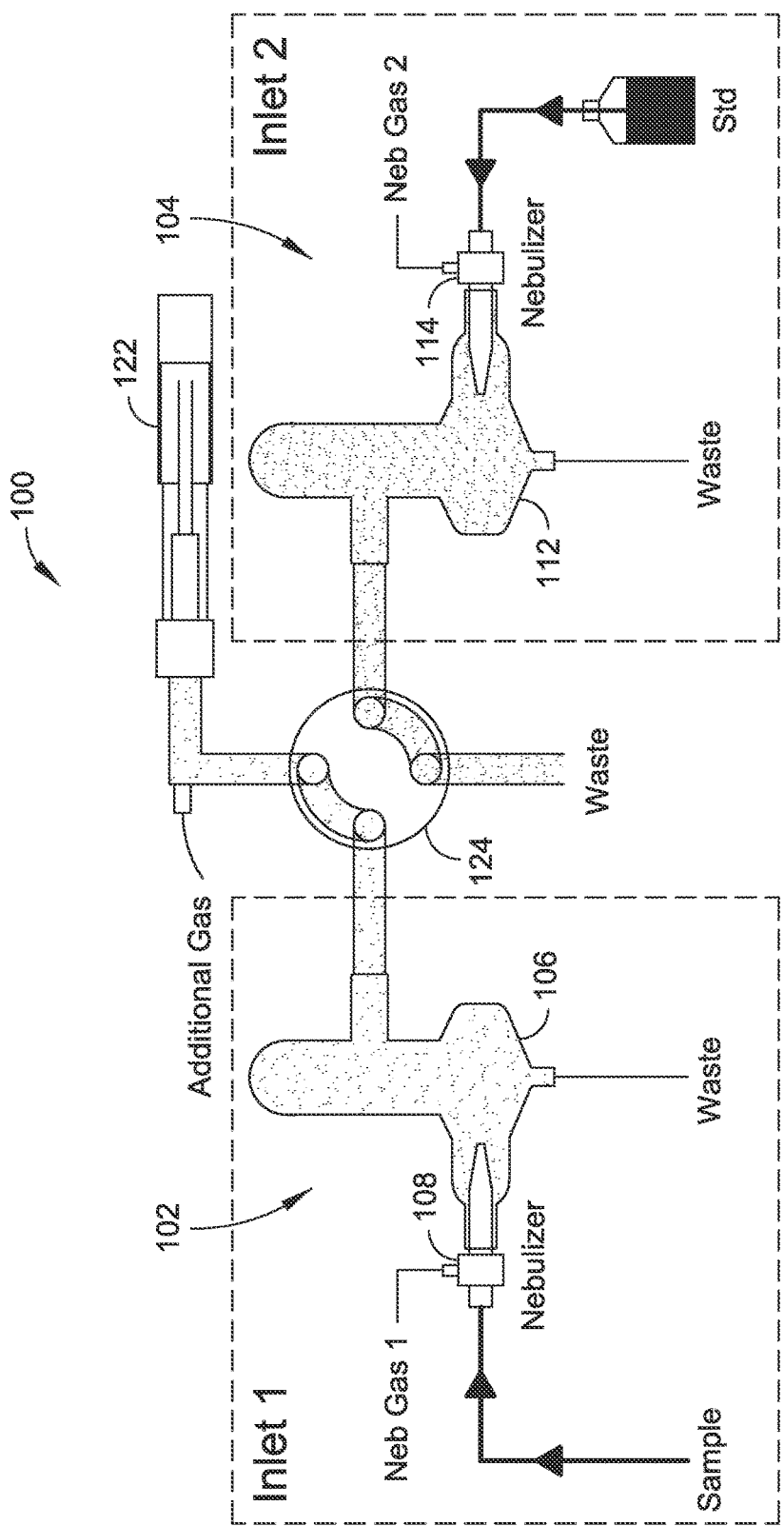
Figure 4:
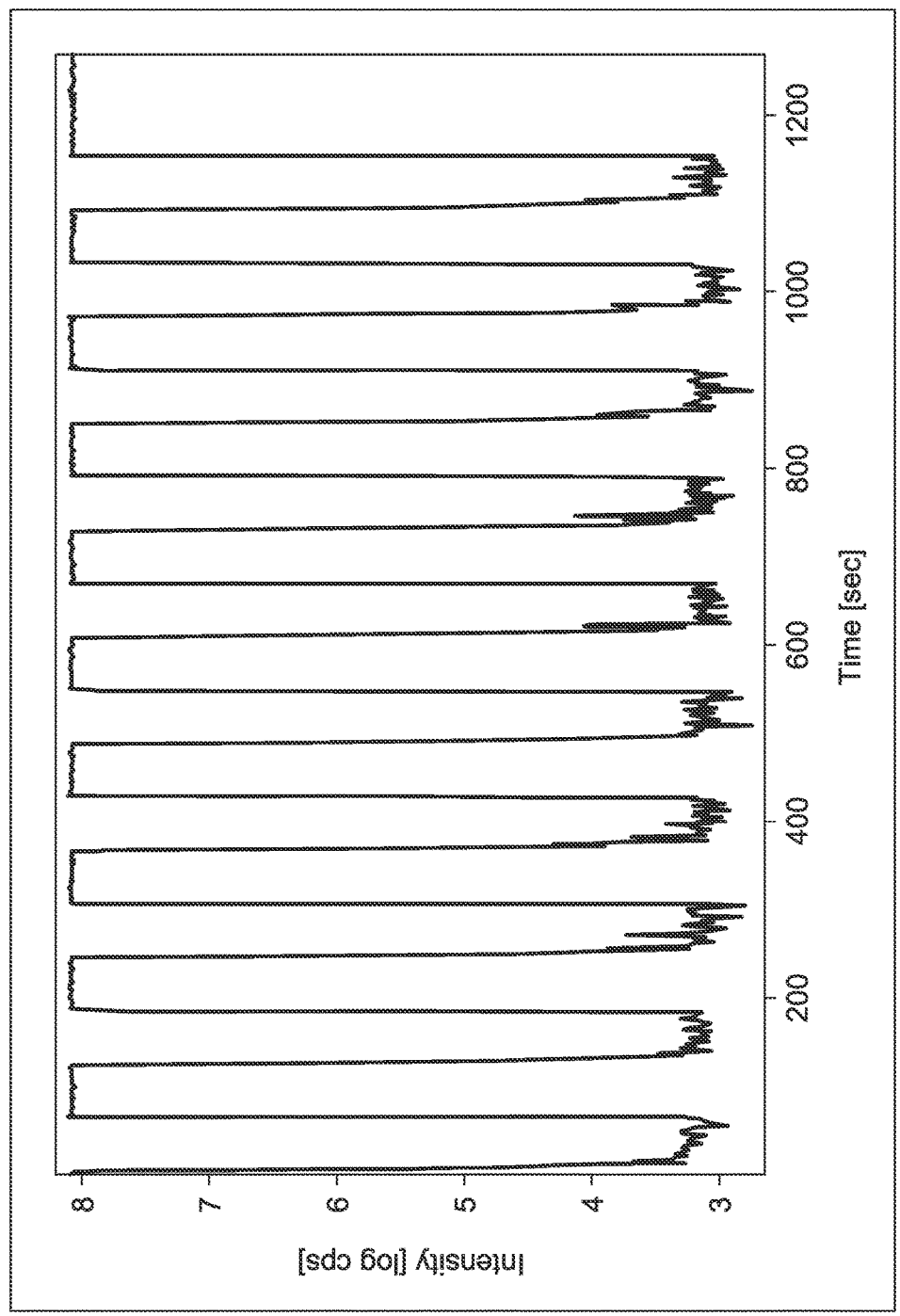
Figure 5:
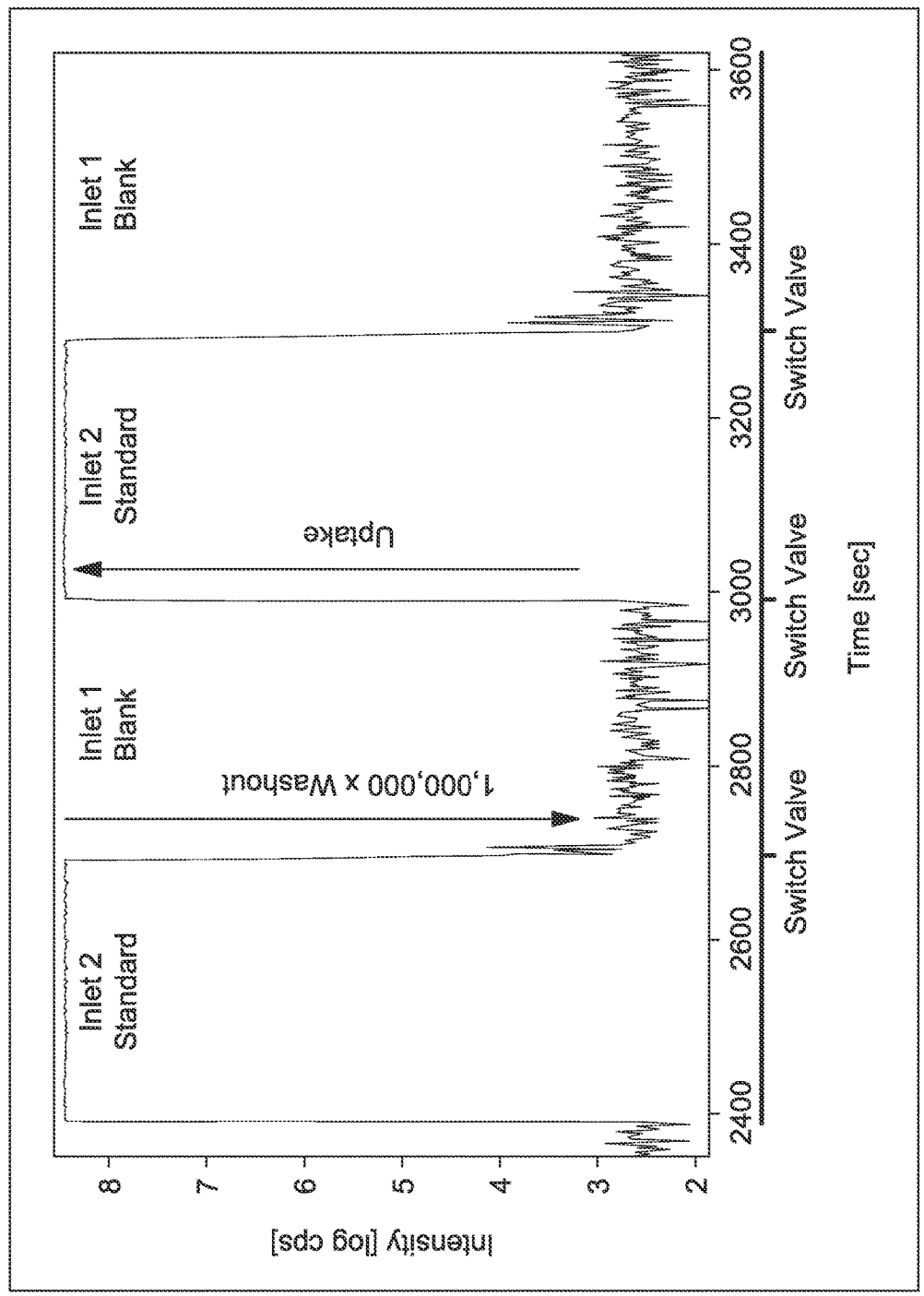
Figure 6:
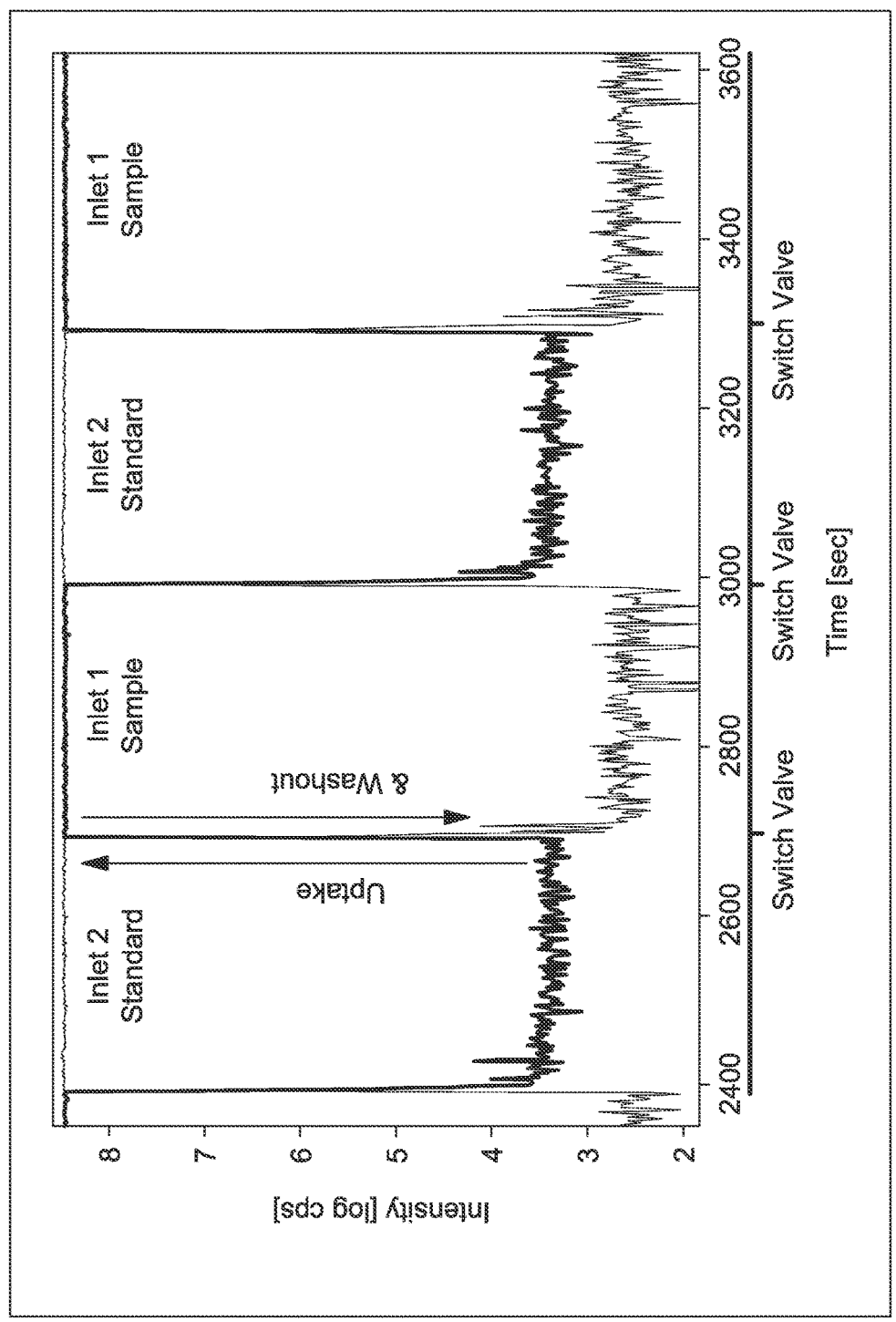
Figure 7:
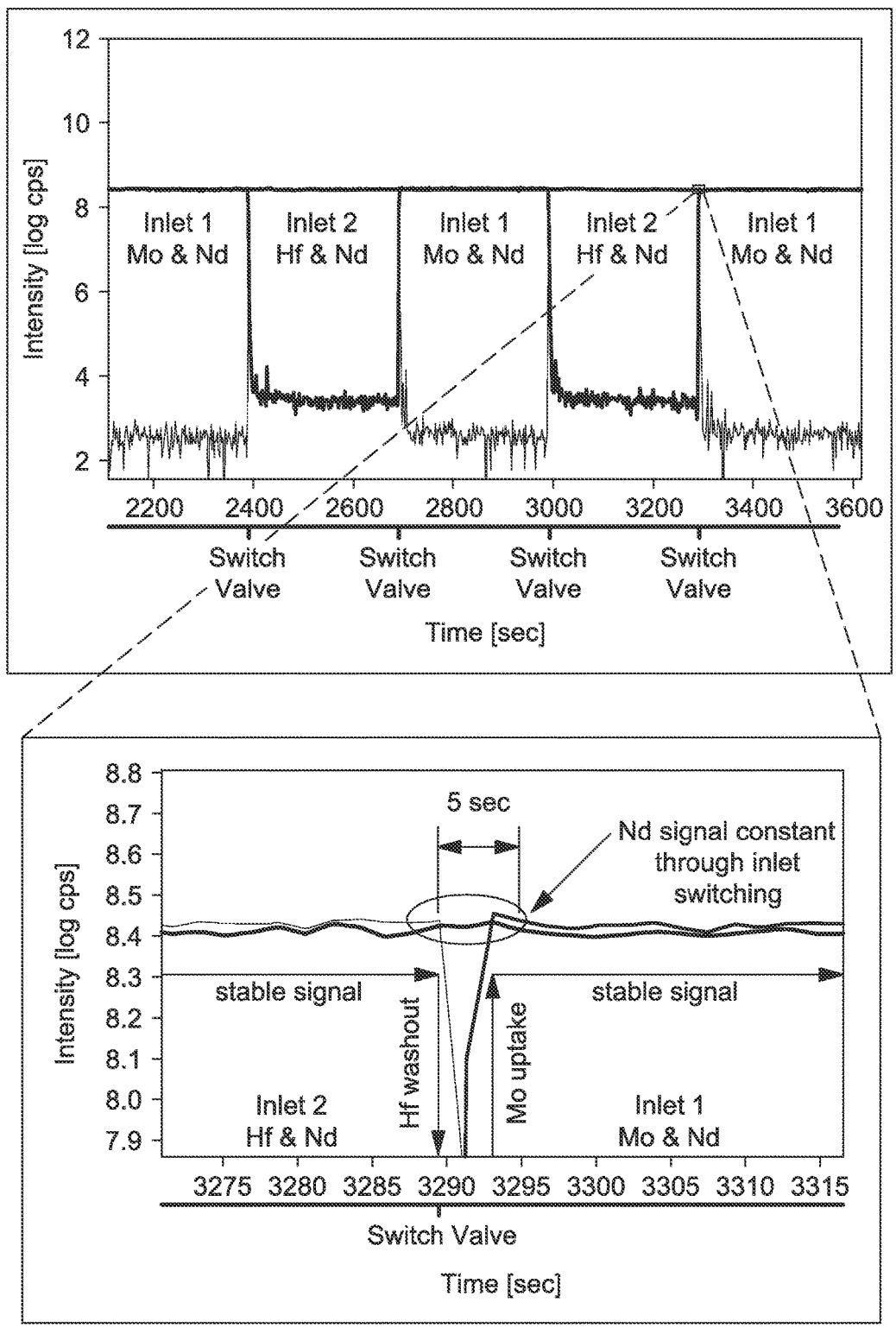
Figure 8:
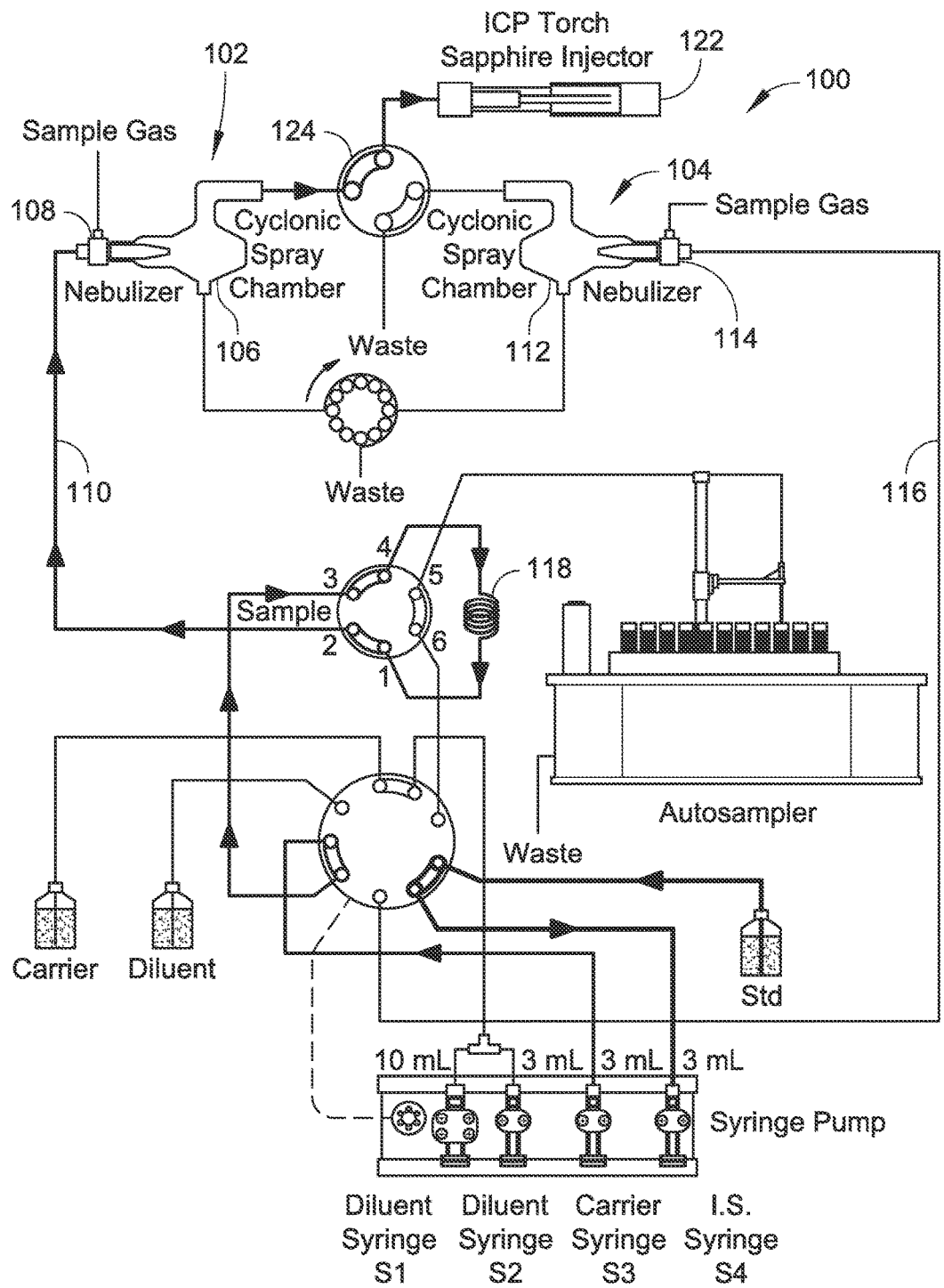
FIG. 8 is a diagrammatic illustration of a system providing balanced duo sample introduction, where the system is configured to supply a sample to a torch while a standard is loaded in accordance with an example embodiment of the present disclosure.
Figure 9:
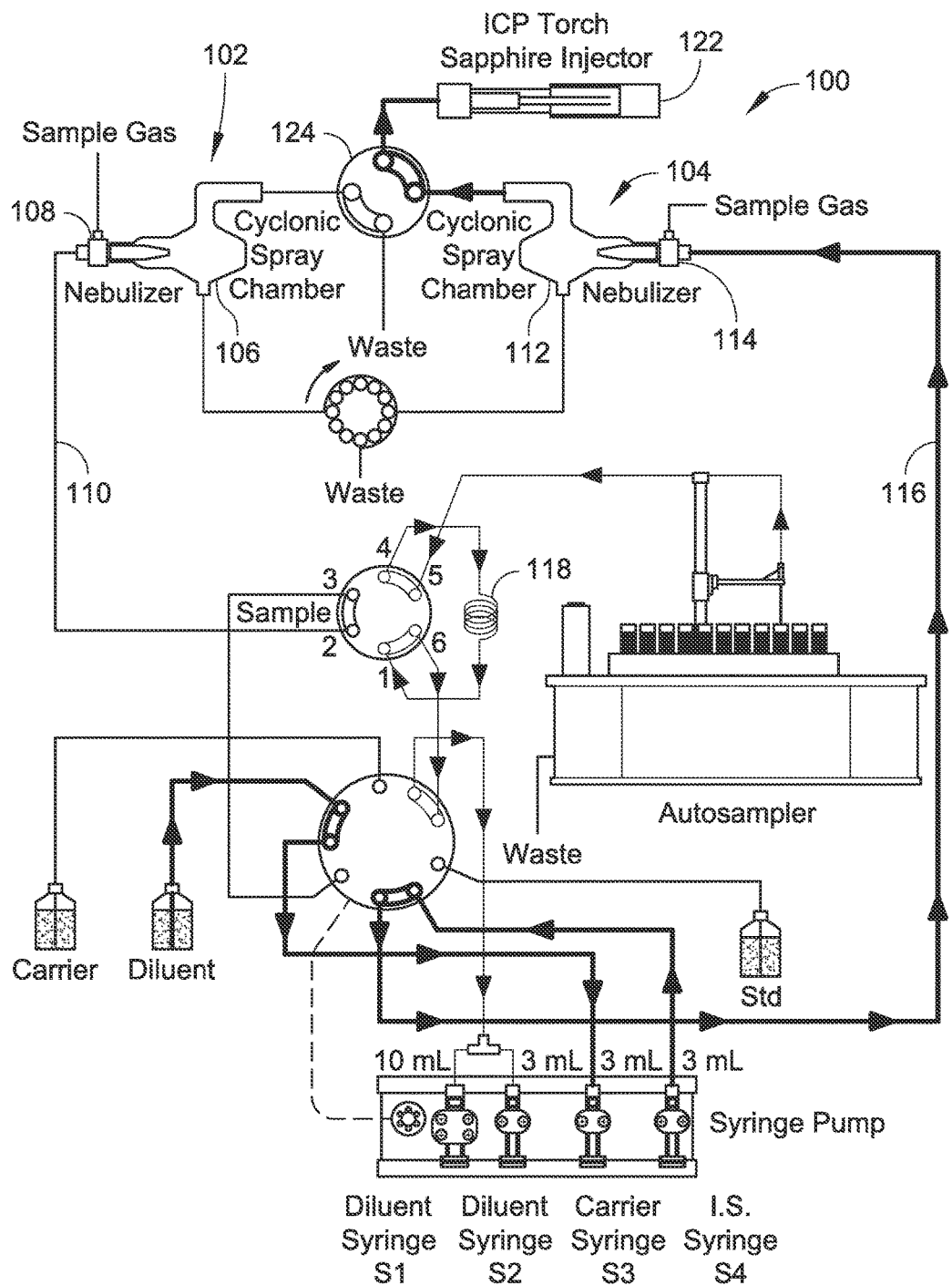
FIG. 9 is a diagrammatic illustration of the system illustrated in FIG. 8, where the system is configured to supply the standard to the torch while a sample is loaded.

Multiple collector inductively coupled plasma mass spectrometry (MC-ICPMS/MC-ICP-MS) can improve upon the precision achievable by ICP-MS during isotope-ratio measurements. For example, an MC-ICPMS system combines an ICP source, an energy filter, a magnetic sector analyzer, and multiple collectors for the measurement of ions. MC-ICPMS equipment can be used to measure the isotopic ratios of elements in geochronologic applications, thermochronologic applications, radiogenic isotopic applications, stable isotopic applications, and so forth. When samples are analyzed using MC-ICPMS equipment, the time required to measure an isotope ratio for a particular sample can range from about four minutes (4 min.) to about five minutes (5 min.). For example, sample solution is introduced to a plasma torch at a flow rate of about one hundred microliters per minute (100 μL/min.). Each sample travels within a sample probe to a spray chamber and then to the torch.

Between successive flows of sample solution to the spray chamber, the samples are typically alternated with washout solution. For MC-ICPMS applications, high levels of washout are typically achieved with a washout of about six-orders of magnitude. This magnitude of washout can also take between about four minutes (4 min.) and about five minutes (5 min.). Further, measurements obtained using MC-ICPMS equipment typically vary with respect to time (e.g., drifting in isotope ratio versus time). Thus, it is generally desirable to perform corrections using a standard to obtain precise isotope ratio measurements. When standard is introduced between each sample, the throughput time to obtain an isotope ratio measurement can be about twenty-five minutes (25 min.) (e.g., about five minutes (5 min.) for washout and uptake of standard, five minutes (5 min.) to measure the standard, five minutes (5 min.) for washout and uptake of sample, five minutes (5 min.) to measure the sample, another five minutes (5 min.) for washout, and so forth).

The present disclosure is directed to a balanced sample introduction system and techniques for providing balanced sample introduction. For example, a balanced duo sample introduction system provides increased throughput and accuracy for applications including, but not necessarily limited to: ICP-MS, ICP-AES, MC-ICPMS, and so forth. In some embodiments, a balanced duo sample introduction system is used for high precision isotope ratio determination for MC-ICPMS, and allows for precise correction for drift in isotope ratio with respect to time. As described herein, the behavior of an example ICP-MS system is at least substantially identical (within analytical precision of the method) between successive samples. In some embodiments, the throughput time to obtain an isotope ratio measurement can be about ten minutes (10 min.) (e.g., about five seconds (5 sec.) to six seconds (6 sec.) or less for uptake of standard, about five minutes (5 min.) to measure standard during washout and uptake of sample, about five seconds (5 sec.) to six seconds (6 sec.) or less for a six-orders of magnitude washout, about five seconds (5 sec.) to six seconds (6 sec.) or less for uptake of sample, about five minutes (5 min.) to measure sample (e.g., during washout and uptake of standard), about five seconds (5 sec.) to six seconds (6 sec.) or less for another six-orders of magnitude washout, and so forth). Further, techniques and systems described herein can quickly select between sample and standard, allowing for more accurate prediction of changes in measurements with respect to time. In this manner, the effects of instrument drift on isotope ratio measurement precision can be reduced. In embodiments of the disclosure, the systems and techniques described herein can furnish sample analysis with little or no uptake and washout time, which can greatly improve the frequency of sample standard bracketing (e.g., for mass bias correction, and so forth). In some embodiments, the systems and techniques described herein can also provide minimal dead volume and/or can be temperature controlled.

Referring generally to FIGS. 1 through 9 systems 100 are described. A system 100 includes a first aerosolization device 102 configured to furnish aerosol and a second aerosolization device 104 configured to furnish aerosol. For example, the first aerosolization device 102 comprises a first spray chamber 106 (e.g., a cyclonic spray chamber) and/or a first desolvation device (e.g., a high sensitivity desolvation device) in fluid communication with a first nebulizer 108. The first nebulizer 108 is coupled with a first sample path 110 and configured to receive fluid from the first sample path 110. Similarly, the second aerosolization device 104 comprises a second spray chamber 112 (e.g., a cyclonic spray chamber) and/or a second desolvation device (e.g., a high sensitivity desolvation device) in fluid communication with a second nebulizer 114. The second nebulizer 114 is coupled with a second sample path 116 and configured to receive fluid from the second sample path 116. The first spray chamber 106 and/or desolvation device and the second spray chamber 112 and/or desolvation device are configured to aerosolize fluid supplied from the first sample path 110 and the second sample path 116, respectively.

The first aerosolization device 102 is balanced with the second aerosolization device 104. For example, the first nebulizer 108 and the first spray chamber 106 and/or desolvation device are balanced with the second nebulizer 114 and the second spray chamber 112 and/or desolvation device. In some embodiments, the first spray chamber 106 and the second spray chamber 112 each comprise a stable sample introduction spray chamber, e.g., where aerosol enters a second homogenization chamber. Further, the first spray chamber 106 and the second spray chamber 112 can each have an internal baffle. The first sample path 110 can also be balanced with the second sample path 116. For example, the first sample path 110 and the second sample path 116 can be balanced in backpressure (e.g., where each sample path is maintained at substantially the same backpressure, which can range between at least approximately two kilopascals (2 kPa) and five kilopascals (5 kPa) in some embodiments).

In some embodiments, the system 100 includes a first pump (e.g., one or more syringe pumps, such as syringe S3 described with reference to FIG. 1) coupled with the first aerosolization device 102 for supplying fluid to the first aerosolization device 102, and a second pump (e.g., one or more syringe pumps, such as syringe S4 described with reference to FIG. 1) coupled with the second aerosolization device 104 for supplying fluid to the second aerosolization device 104. The first pump and the second pump can also be balanced. For instance, the first pump and the second pump can be balanced to stable forward flow rates using high tolerance manufacturing techniques (e.g., where each pump furnishes fluid at substantially the same flow rate, which can range between at least approximately ten microliters per minute (10 μL/min.) and one hundred microliters per minute (100 μL/min.) in some embodiments). As described with reference to FIG. 1, syringe S1 can fill a first sample loop 118 while syringe S4 dispenses a second sample loop 120, then syringe S3 can dispense the first sample loop 118 while syringe S2 fills the second sample loop 120, and so on.

In embodiments of the disclosure, the nebulizers, spray chambers, desolvation devices, sample paths, pumps, and so forth are balanced by matching characteristics of corresponding components. For example, quality control is maintained during manufacturing of the first nebulizer 108 and the second nebulizer 114. Further, the lengths of tubing used for the first sample path 110 and the second sample path 116 are substantially the same, and the tubing has substantially the same inside diameters. Additionally, vacuums are applied to the first nebulizer 108 and the second nebulizer 114 that are substantially the same, generating substantially the same flow rates of fluid into the nebulizers. For example, one or more syringe pumps are used to fill sample loop 118 (and possibly sample loop 120) accurately and precisely. Still further, aerosol transport efficiencies of the first spray chamber 106 and the second spray chamber 112 are at least substantially the same. In this manner, accurate volumes and accurate flow rates are achieved in a system 100. In some embodiments, balance within a system 100 is measured by obtaining fluid from the same solution through both the first sample path 110 and the second sample path 116, and the results are compared. In this manner, balance within the system can be verified (e.g., within analytical precision of the method).

The first aerosolization device 102 and the second aerosolization device 104 are coupled with an output configured to supply the aerosol from the first aerosolization device 102 and/or the second aerosolization device 104 (e.g., to an ICP torch 122). For example a selection device (e.g., a selection valve 124) couples the first aerosolization device 102 and the second aerosolization device 104 to the output. The selection valve 124 is configured to selectively provide aerosol from the first aerosolization device 102 and/or the second aerosolization device 104 to the output. In some embodiments, the selection valve 124 is configured to select between sample supplied to the ICP torch 122 and standard supplied to the ICP torch 122. The selection valve 124 can be a high speed valve, which can quickly switch between aerosol supplied from the first aerosolization device 102 and the second aerosolization device 104.

When aerosol is supplied from one aerosolization device of a system 100, another aerosolization device can be stopped, sent to waste, and so forth. For example, standard is sent to waste while sample is supplied, standard is stopped while sample is supplied, supplies of sample and standard are quickly alternated, and so forth. Further, in some embodiments, standard can be continuously provided by one aerosolization device and sent to waste between standard measurements. In some example implementations, sample and standard are alternated between about every ten seconds (10 sec.) and thirty seconds (30 sec.). Further, sample and standard can be alternated between about twenty times (20×) and one hundred times (100×). However, these values are provided by way of example only and are not meant to limit the disclosure. In other embodiments, sample and standard are alternated at different rates and/or different numbers of times, and so forth.

In embodiments of the disclosure, the selection valve 124 is connected to waste with waste path tubing that includes a restriction 126. For example, the waste tubing has the same or substantially the same diameter as tubing that extends to the ICP torch 122 from the selection valve 124 (e.g., to achieve the same or substantially the same friction, pressure, and so forth). In this manner, the waste path can be balanced with the output. The restriction 126 can enable aerosol furnished to the ICP torch 122 to stabilize faster. Further, in some embodiments, make up gas 128, e.g., Argon (Ar), can be supplied to the ICP torch 122 to maintain stable plasma. For instance, make up gas 128 can be supplied at a flow rate that can range between at least approximately two hundred milliliters per minute (200 mL/min.) and four hundred milliliters per minute (400 mL/min.). In some embodiments, a system 100 can also include a reservoir 130, which can be coupled with the sample loop 118 and/or the second sample loop 120.

It should be noted that the duo sample introduction systems 100 are provided by way of example only and is not meant to limit the present disclosure. Thus, in other embodiments more than two aerosolization devices can be coupled with the selection valve 124 (e.g., three (3) aerosolization devices, four (4) aerosolization devices, and so forth). For example, in some embodiments, a system 100 includes a third aerosolization device configured to furnish aerosol to the ICP torch 122. The third aerosolization device comprises a third spray chamber (e.g., a cyclonic spray chamber) in fluid communication with a third nebulizer. The third nebulizer is coupled with a third sample path and configured to receive fluid from the third sample path. In this configuration, the output is coupled with the third aerosolization device, and the selection valve 124 is configured to selectively provide aerosol from the first aerosolization device 102, the second aerosolization device 104, and/or the third aerosolization device to the output.

A procedure is described in an example implementation in which a balanced sample introduction system is used for an application such as ICP-MS, ICP-AES, MC-ICPMS, and so forth. A first aerosol is furnished to a torch using a first aerosolization device during a first time interval. For example, with reference to FIGS. 1 and 2, aerosolized internal standard is supplied to the ICP torch 122 from the first spray chamber 106. Then, a second aerosol is furnished to the torch via a second aerosolization device during a second time interval subsequent to the first time interval, where the first aerosolization device 102 is balanced with the second aerosolization device 104. For example, with continuing reference to FIGS. 1 and 2, aerosolized sample is supplied to the ICP torch 122 from the second spray chamber 112, which is balanced with the first spray chamber 106. In some embodiments, the second aerosolization device 104 is washed out during at least a portion of the first time interval while the first fluid is provided to the torch. For instance, with continuing reference to FIGS. 1 and 2, the second spray chamber 112 is washed out while the aerosolized standard is supplied from the first spray chamber 106.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A system comprising:
a first aerosolization device configured to furnish a first aerosol;

a second aerosolization device configured to furnish a second aerosol, the first aerosolization device balanced with the second aerosolization device by at least one of matching backpressure characteristics of a first sample path associated with the first aerosolization device with a second sample path associated with the second aerosolization device, matching forward flow rate characteristics of a first pump associated with the first aerosolization device with a second pump associated with the second aerosolization device, matching length characteristics of first tubing associated with the first aerosolization device with second tubing associated with the second aerosolization device, or matching inside diameter characteristics of first tubing associated with the first aerosolization device with second tubing associated with the second aerosolization device;

an output coupled with the first aerosolization device and the second aerosolization device, the output configured to supply at least one of the first aerosol or the second aerosol; and a selection device comprising a valve coupling the first aerosolization device and the second aerosolization device to the output, the selection device configured to selectively provide at least one of the first aerosol or the second aerosol to the output.

2. The system as recited in claim 1, further comprising a waste path balanced with the output, wherein the selection device is coupled with the waste path.

3. The system as recited in claim 1, wherein the first aerosolization device comprises a first nebulizer configured to receive a fluid from a sample path and at least one of a spray chamber or a desolvation device in fluid communication with the first nebulizer, the at least one of the spray chamber or the desolvation device configured to aerosolize the fluid to form the first aerosol.

4. The system as recited in claim 3, wherein the second aerosolization device comprises a second nebulizer configured to receive a second fluid from a second sample path and a second spray chamber in fluid communication with the second nebulizer, the second spray chamber configured to aerosolize the second fluid to form the second aerosol, wherein the second nebulizer is balanced with the first nebulizer by matching characteristics of the first nebulizer with the second nebulizer.

5. The system as recited in claim 1, further comprising a torch coupled with the output for receiving the at least one of the first aerosol or the second aerosol.

6. The system as recited in claim 1, further comprising a first pump coupled with the first aerosolization device for furnishing a first fluid to the first aerosolization device and a second pump coupled with the second aerosolization device for furnishing a second fluid to the second aerosolization device, wherein the first pump and the second pump are balanced by matching characteristics of the first pump with the second pump.

7. The system as recited in claim 6, wherein the first pump comprises a first syringe pump and the second pump comprises a second syringe pump.

8. The system as recited in claim 1, further comprising a third aerosolization device configured to furnish a third aerosol, wherein the output is coupled with the third aerosolization device, and the selection device is configured to selectively provide at least one of the first aerosol, the second aerosol, or the third aerosol to the output.

9. A system comprising:
a first nebulizer configured to receive a first fluid from a first sample path;

a first spray chamber in fluid communication with the first nebulizer, the first spray chamber configured to aerosolize the first fluid to form a first aerosol;

a second nebulizer configured to receive a second fluid from a second sample path;

a second spray chamber in fluid communication with the second nebulizer, the second spray chamber configured to aerosolize the second fluid to form a second aerosol, the first nebulizer, the first spray chamber, and the first sample path balanced with the second nebulizer, the second spray chamber, and the second sample path by matching characteristics of the first nebulizer with the second nebulizer, the first sample path with the second sample path, and the first spray chamber with the second spray chamber;

an output coupled with the first spray chamber and the second spray chamber, the output configured to supply at least one of the first aerosol or the second aerosol to a torch; and a selection valve coupling the first spray chamber and the second spray chamber to the output, the selection valve configured to selectively provide at least one of the first aerosol or the second aerosol to the output.

10. The system as recited in claim 9, further comprising a waste path balanced with the output, wherein the selection valve is coupled with the waste path.

11. The system as recited in claim 9, further comprising a first pump coupled with the first sample path for furnishing the first fluid to the first nebulizer and a second pump coupled with the second sample path for furnishing the second fluid to the second nebulizer, wherein the first pump and the second pump are balanced by matching characteristics of the first pump with the second pump.

12. The system as recited in claim 11, wherein the first pump comprises a first syringe pump and the second pump comprises a second syringe pump.

13. The system as recited in claim 9, further comprising a third nebulizer configured to receive a third fluid from a third sample path; and a third spray chamber in fluid communication with the third nebulizer, the third spray chamber configured to aerosolize the third fluid to form a third aerosol, wherein the output is coupled with the third spray chamber, and the selection valve is configured to selectively provide at least one of the first aerosol, the second aerosol, or the third aerosol to the output.

14. A method comprising:
furnishing a first aerosol to a torch using a first aerosolization device during a first time interval;

furnishing a second aerosol to the torch via a second aerosolization device during a second time interval subsequent to the first time interval, wherein the first aerosolization device is balanced with the second aerosolization device by at least one of matching backpressure characteristics of a first sample path associated with the first aerosolization device with a second sample path associated with the second aerosolization device, matching forward flow rate characteristics of a first pump associated with the first aerosolization device with a second pump associated with the second aerosolization device, matching length characteristics of first tubing associated with the first aerosolization device with second tubing associated with the second aerosolization device, or matching inside diameter characteristics of first tubing associated with the first aerosolization device with second tubing associated with the second aerosolization device; and selectively providing at least one of the first aerosol or the second aerosol to the torch by a selection valve coupling the first aerosolization device and the second aerosolization device to the torch.

15. The method as recited in claim 14, further comprising supplying gas to the torch to maintain a stable plasma at the torch.

16. The method as recited in claim 14, further comprising washing out the second aerosolization device during at least a portion of the first time interval while the first fluid is provided to the torch.

17. The method as recited in claim 14, wherein the first aerosol comprises a standard and the second aerosol comprises a sample.

18. The method as recited in claim 14, wherein the first aerosolization device comprises a nebulizer configured to receive a fluid from a sample path and at least one of a spray chamber or a desolvation device in fluid communication with the nebulizer, the at least one of the spray chamber or the desolvation device configured to aerosolize the fluid to form the first aerosol.

19. The method as recited in claim 14, wherein furnishing a first aerosol to a torch using a first aerosolization device comprises using a first pump coupled with the first aerosolization device to furnish a first fluid to the first aerosolization device, and furnishing a second aerosol to the torch via the second aerosolization device comprises using a second pump coupled with the second aerosolization device to furnish a second fluid to the second aerosolization device, wherein the first pump and the second pump are balanced by matching characteristics of the first pump with the second pump.

20. The method as recited in claim 19, wherein the first pump comprises a first syringe pump and the second pump comprises a second syringe pump.

* * * * *